United States Patent
Pongpairochana

(10) Patent No.: US 8,992,472 B2
(45) Date of Patent: Mar. 31, 2015

(54) AUTOMATIC INJECTION DEVICE

(76) Inventor: Vincent Pongpairochana, La Conversion (CH)

( * ) Notice: Subject to any disclaimer, the term of this patent is extended or adjusted under 35 U.S.C. 154(b) by 545 days.

(21) Appl. No.: 13/262,676

(22) PCT Filed: Oct. 16, 2009

(86) PCT No.: PCT/EP2009/063598
§ 371 (c)(1),
(2), (4) Date: Oct. 3, 2011

(87) PCT Pub. No.: WO2010/112090
PCT Pub. Date: Oct. 7, 2010

(65) Prior Publication Data
US 2012/0035542 A1 Feb. 9, 2012

(30) Foreign Application Priority Data
Apr. 2, 2009 (EP) .................................... 09157227

(51) Int. Cl.
| A61M 5/00 | (2006.01) |
| A61M 5/20 | (2006.01) |
| A61M 5/24 | (2006.01) |
| A61M 5/32 | (2006.01) |
| G06F 19/00 | (2011.01) |
| A61M 5/315 | (2006.01) |
| A61M 5/48 | (2006.01) |

(52) U.S. Cl.
CPC . *A61M 5/20* (2013.01); *A61M 5/24* (2013.01); *A61M 5/3202* (2013.01); *G06F 19/3468* (2013.01); *A61M 5/31525* (2013.01); *A61M 5/31546* (2013.01); *A61M 5/3204* (2013.01); *A61M 5/326* (2013.01); *A61M 5/3287* (2013.01); *A61M 5/482* (2013.01); *A61M 2005/206* (2013.01); *A61M 2005/2073* (2013.01); *A61M 2005/2407* (2013.01); *A61M 2005/2496* (2013.01); *A61M 2205/3334* (2013.01); *A61M 2205/3553* (2013.01); *A61M 2205/3561* (2013.01); *A61M 2205/3584* (2013.01); *A61M 2205/52* (2013.01); *A61M 2205/6072* (2013.01); *A61M 2205/8206* (2013.01)

USPC ................ 604/110; 604/131; 700/237; 705/3

(58) Field of Classification Search
USPC ........ 604/110, 131, 136, 192; 700/237; 705/3
See application file for complete search history.

(56) References Cited

U.S. PATENT DOCUMENTS

| 7,072,738 B2 * | 7/2006 | Bonney et al. ................ 700/237 |
| 2009/0131875 A1 * | 5/2009 | Green ........................... 604/187 |
| 2009/0240210 A1 * | 9/2009 | Walton et al. ................. 604/196 |

FOREIGN PATENT DOCUMENTS

| EP | 0 108 529 | 5/1984 |
| WO | 2004/098687 | 11/2004 |
| WO | 2005/077441 | 8/2005 |

OTHER PUBLICATIONS

International Search Report dated Apr. 27, 2010, corresponding to PCT/EP2009/063598.
European Search Report dated Sep. 8, 2009, corresponding to priority application No. EP 09 15 7227.

* cited by examiner

*Primary Examiner* — Theodore Stigell
(74) *Attorney, Agent, or Firm* — Young & Thompson

(57) ABSTRACT

An injection device (22) is equipped with a compartment articulated with reference to the device to receive a syringe (10) with staked needle (18) protected by a protection cap (20) coupled with the syringe, the compartment being susceptible to evolve from a first open position for the insertion and the removal of the syringe, and a second closed position for the realization of the injection. The device includes a detachment system intended to cooperate with the cap of the syringe to decouple it from the syringe, the detachment being conditioned by the passage of the compartment to its second position. Furthermore, the passage of the compartment from the second to the first position is conditioned by the coupling of the cap.

31 Claims, 15 Drawing Sheets

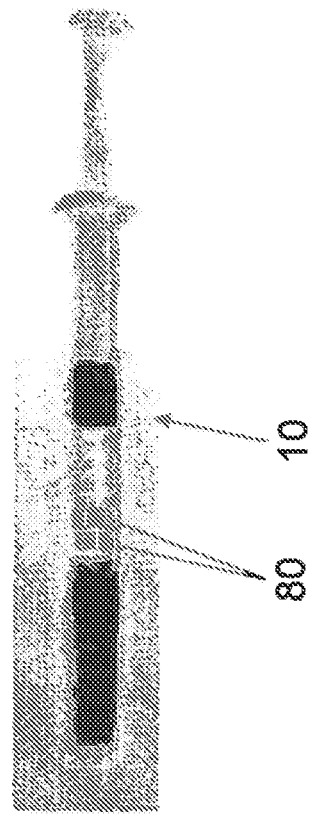
FIG. 11
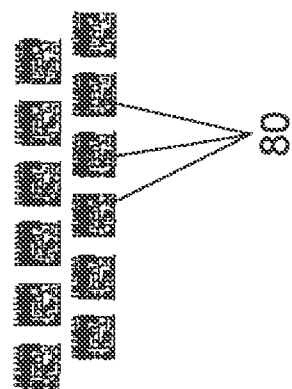

AUTOMATIC INJECTION DEVICE

TECHNICAL FIELD

The present invention relates to an injection device, equipped with a compartment articulated in reference to the device and designed to receive a syringe with a staked needle protected by a needle shield cap. The compartment is susceptible to evolve from a first open position for the insertion and the removal of the syringe, and a second closed position for the realization of the injection.

BACKGROUND ART

Many treatments require that patients undergo frequent intramuscular or subcutaneous injections at regular intervals e.g. daily, weekly or monthly. To allow a patient to live a normal life it is common that he performs the injections himself. For this reason, several devices have been developed with the particular aim to facilitate the injection process, for ergonomic as much as psychological reasons. About the latter, one can easily conceive that the vision of the needle can frighten a patient. Furthermore, the risk of injury or of contamination is critical, in particular for other persons having to handle the devices.

To improve the safety of syringes, passive or active protection caps have been developed, allowing the needle to be hidden. Nevertheless, this type of device brings no improvement to the functionality of the injection process and it is always for the patient, as with conventional syringes, to carry out manually the injection process.

Some automatic injection devices offer a substitute for the patient in carrying out automatically the injection, after it is triggered. There is in this way disposable devices. Their cost is a major inconvenience in the case of treatment requiring frequent injections. Furthermore, given that the device is single use, it is technically unsophisticated, in particular from the controls point of view, or from the electronic means that allow improvements to the functionalities.

Devices use sometime conventional syringes, which is advantageous, because it allows for the combination of disposable components for the parts in contact with the medication, and components that can be perfected, because they are being kept from one utilization to another. The treatment protocols are generally conceived so that the entire content of the syringe is injected in a single time. However, it is necessary to perform many handling steps, before the injection, to remove the cap protecting the syringe, introduce the syringe into the device, then, after the injection, to remove the syringe from the device and replace the cap. This type of device has the inconvenience that certain of the handling steps have to be carried out while the needle is not protected. The handling of the used syringe and contaminated after injection exposes the hospital personnel or people surrounding the patient to risks of infection.

Another type of device uses multi-dose cartridges of medication, which is susceptible to be used several times consecutively, the apparatus taking care to administer the correct quantity to the patient. This type of apparatus can be safe for the patient and the persons handling it, because the injection needle is always hidden and does not present a risk of injury. This type of apparatus is particularly sophisticated, in particular to ensure in a safe way the dosage of medication, but also to ensure its programming, depending on the treatment and the medication. These apparatus are adapted for multi-dose cartridges, but cannot receive conventional syringes.

The present invention aims to offer a device allowing the combination of the advantages of the above apparatus, whilst avoiding the inconveniences. Particularly, the invention relates to a very safe device, advantageous from the cost impact on the treatment and which can be coupled with high-performance electronic means.

DISCLOSURE OF THE INVENTION

In a more precise way, the invention relates to an injection device equipped with a compartment articulated in reference to the device to receive a syringe with staked needle protected by a needle shield cap coupled with the syringe. The compartment is susceptible to evolve from a first open position for the insertion and the removal of the syringe, and a second closed position for the realization of the injection. According to the invention and in order to avoid any risk of injury or of contamination with the needle, the device includes a detachment system intended to cooperate with the cap of the syringe for the decoupling from the syringe, the detachment being conditioned by the passage of the compartment to its second position. Furthermore, the passage of the compartment from the second to the first position is conditioned by the coupling of the cap.

The invention relates also to a management system and to the control of the injection protocols, including:
- a server storing data relative to a patient and his treatment, and
- at least a device according to one of the preceding claims to carry out the injections, including means for connecting at distance to the server and electronic means, characterized in that the aforementioned electronic means are arranged to
- record the injections history,
- monitor and control the adherence of the treatment and, eventually, remind the patient of the injection time,
- transfer to the server the aforementioned injections history,
- receive and process information transferred by the server.

Other aspects of the invention are mentioned in the claims of the present application.

BRIEF DESCRIPTION OF THE DRAWINGS

Other characteristics of the present invention will appear more clearly when reading the description that will follow, made in reference to the drawing annexed, where:

the FIGS. 1 to 9 illustrate different successive steps of the utilization of a device according to the invention, the FIGS. 1b and 2b being enlarged views, and the FIG. 10 shows schematically a management system and control of injection protocols, the FIG. 11 illustrates an example of the marking for the identification of a syringe, particularly adapted to a device according the invention, and the FIGS. 12 to 15 show different successive steps of the utilization of a device according to another embodiment of the invention.

BEST MODE(S) FOR CARRYING OUT THE INVENTION

Figure 1:
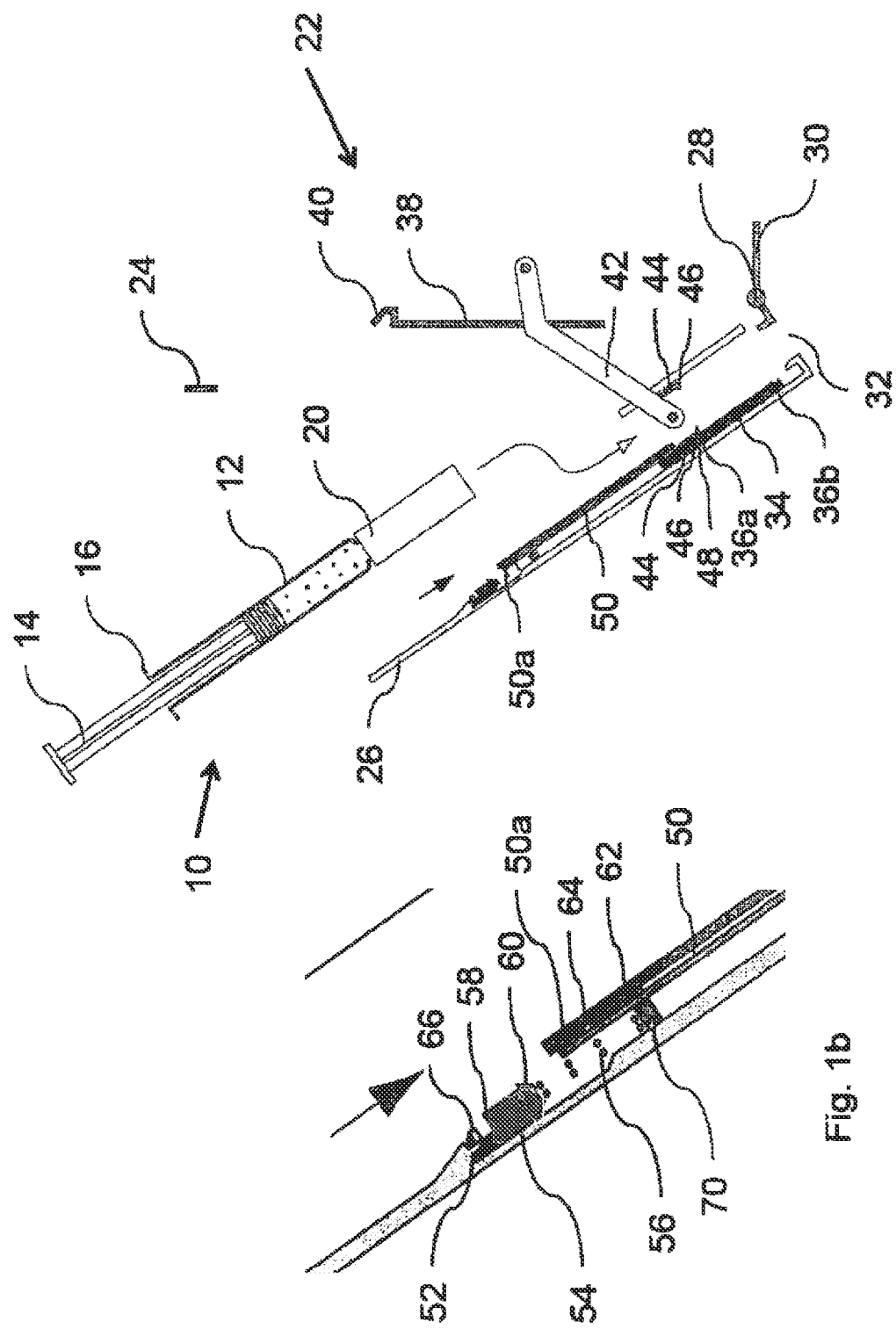
Figure 2:
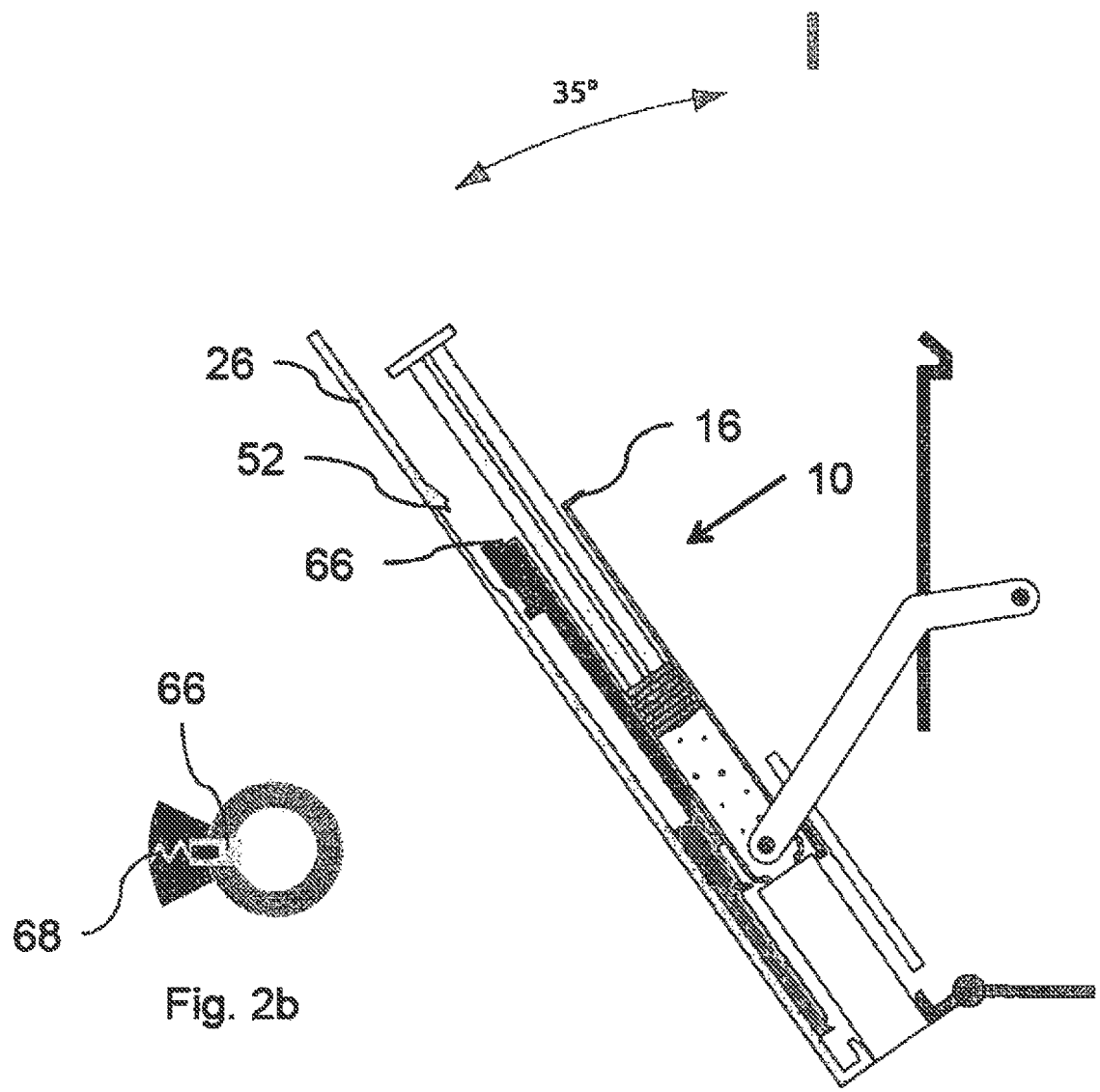
Figure 3:
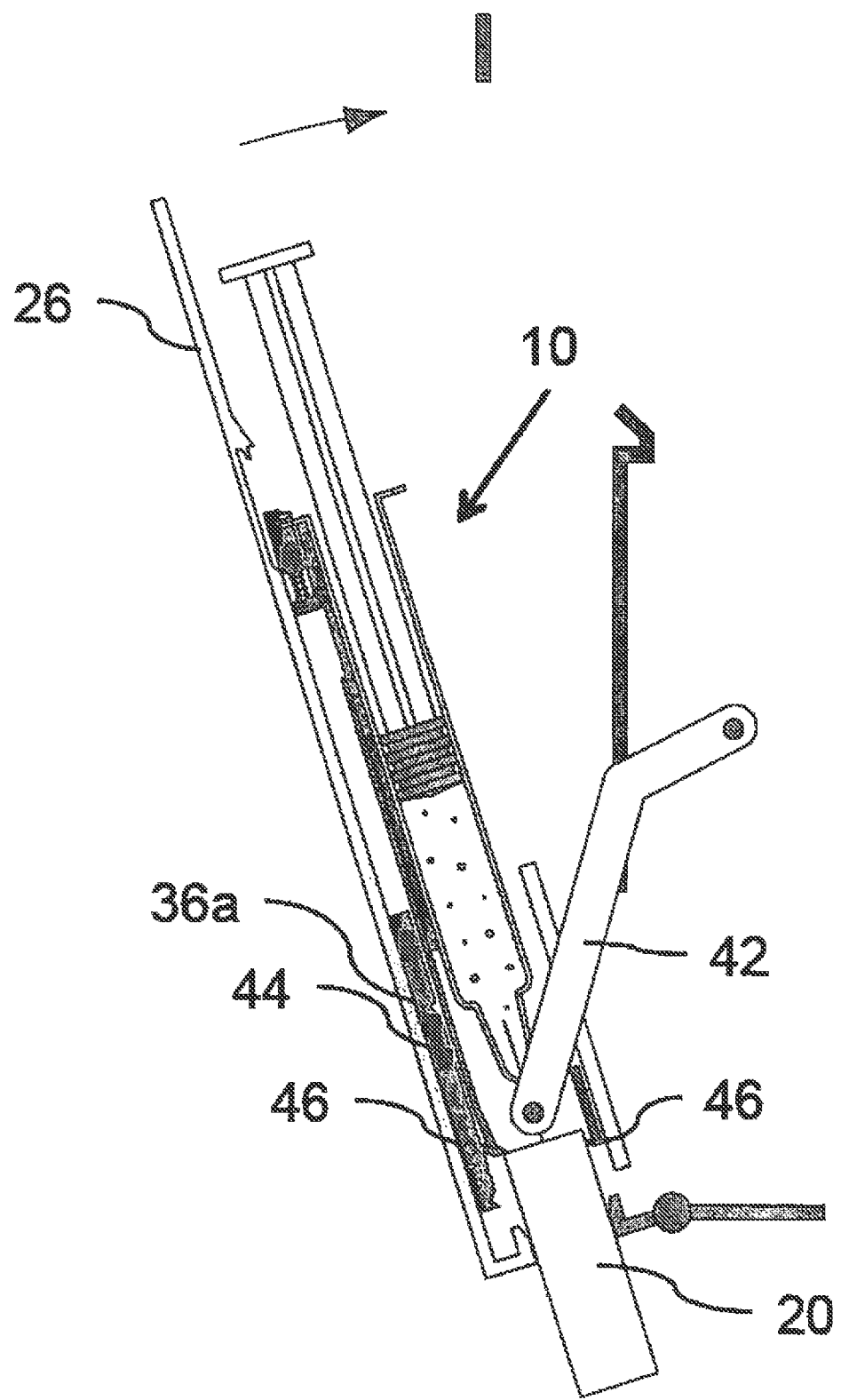
Figure 4:
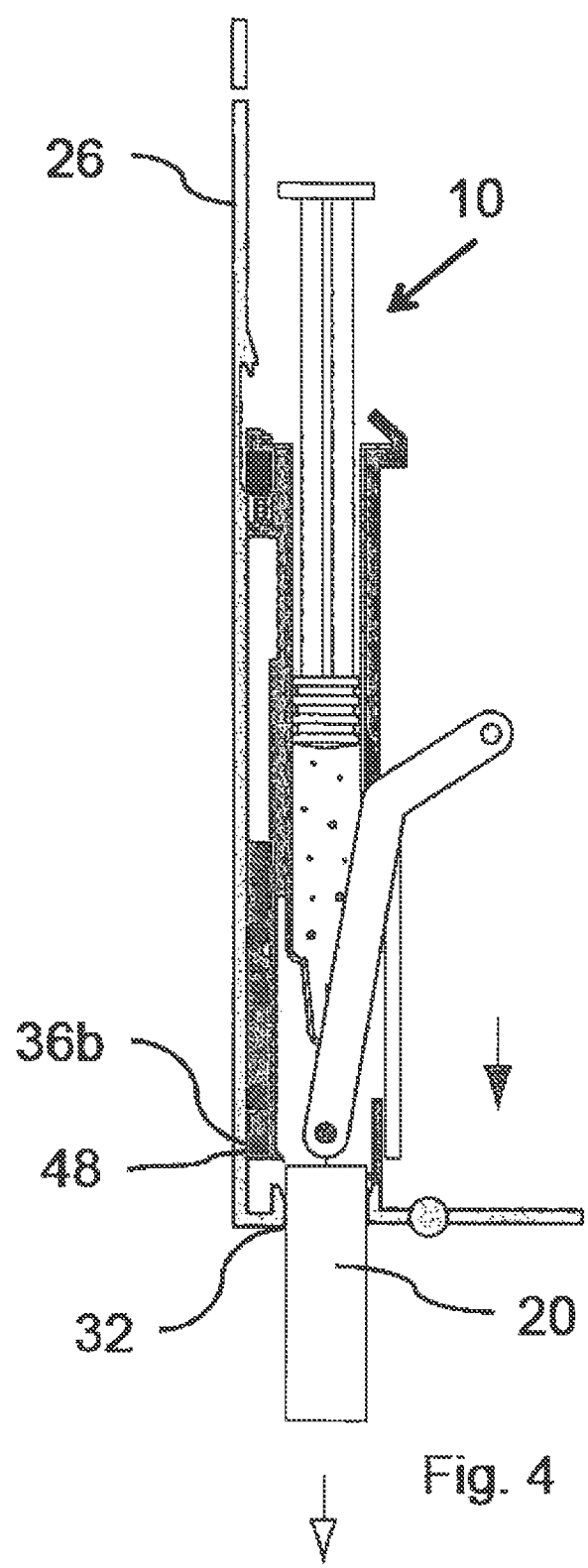

The FIGS. 1 to 9 illustrate, schematically, a device allowing a patient to self inject the content of a syringe 10 of a conventional type. It is meant by conventional syringe, a syringe that includes a barrel 12 inside of which can take place a liquid, that can be compressed by a piston 14 movable inside the barrel. In general, the extremity of barrel 12 receiving the piston is equipped with a flange 16, to provide support for a manual injection. The syringe 10 can receive at the extremity opposite to the flange, a hollow needle 18, to inject the liquid contained in the barrel 12 of the syringe 10, into the patient.

To protect the needle 18, this one being covered, when the syringe 10 is not used, by a cap 20, manufactured in general of rigid plastic, coupled by force to the syringe 10.

On the FIGS. 1 to 9, the device is shown schematically, in order to make the understanding of the invention clearer. In this way, the electronic means controlling the injection, the motors and other screen for the display of information are not shown on the drawings. In order not to overload the drawings, certain components have been shown only in certain Figures.

In this way, FIG. 1 shows an injection device 22 according to the invention, of which a first wall 24 includes a flap 26 articulated on a hinge 28. This hinge is, in preference, located on a second wall 30, adjacent to the first wall 24. One defines in this way a compartment, articulated with reference to the device 22. As one will understand later on, this compartment is intended to receive a syringe 10, for the injection of its content.

The second wall 30 is pierced, in its part belonging to the compartment, by an opening 32 for the passage of the needle 18 of the syringe 10 and of its cap 20. To receive the cap, the compartment includes in addition a guiding tube 34, coupled with the flap 26 and located on the side of the opening 32, so as to guide the syringe 10 in the desired position for its insertion into the compartment and for the injection. The guiding tube 34 presents, on its internal wall, a first channel 36a and a second channel 36b, aligned according to the longitudinal axis of the compartment and distant from one another. The channels 36a and 36b are identical and form a series. Several series can be distributed on the circumference of the internal wall of the guiding tube. The role of these channels 36a and 36b will appear later in the description.

The device includes in addition an internal partition 38 located in the device, in order to perfectly define a housing for the syringe 10. This internal partition 38 presents a shoulder 40 to cooperate with the flange 16 of the syringe 10. The internal partition 38 is arranged so as to extend the guiding tube 34 when the compartment is in a closed position, which is when the flap 26 is aligned with the first wall 24.

An arm 42 is also mounted rotating at a first extremity on the device. A second extremity of the arm 42 is mounted rotating on the compartment, to hold the flap 26 and to define a maximum open position. In this way are defined a first maximum open position for the insertion and the removal of the syringe, and a second closed position for the realization of the injection.

According to an interesting point of the invention, the compartment includes means for detaching the cap in reference to the syringe. These means can be formed by a ring 44 adjusted inside of the guiding tube 34. The second extremity of arm 42 is rotating on the ring 44, so that that the opening and the closing of flap 26 with reference to the device, drives a translation movement of ring 44, respectively in direction of the opening 32 and in direction away from the opening 32.

More precisely, the external diameter of the ring 44 is slightly inferior to the internal diameter of the guiding tube 34, in such a way that their wall, respectively outside and inside, are in contact with each other. The ring 44 includes one or several grippers 46, located in preference at the extremity of the ring 44. The grippers 46 are equipped with a bulge 48 located on the outside wall of ring 44 and with a shape matching channels 36a and 36b. Each gripper is intended to cooperate with the channels of a series. FIG. 1a shows two grippers 46, positioned at different heights with reference to the compartment and, as one will understand hereafter, intended to cooperate differently with cap 20.

The stroke of guiding tube 34 defined by the geometry of arm 42, is equal to the distance separating two channels 36a and 36b of a series. The grippers 46 are positioned in such a way that, when the compartment is in its first maximum open position, the bulges 48 are resting in the firsts channels 36a and when the compartment is in its second closed position, the bulges 48 are resting in the second channels 36b. Naturally, between these two positions, the grippers 46 shift between the two channels 36a and 36b and the bulges 48 are pressed on the internal wall of the guiding tube 34, that constrain slightly the guiding tube 34 and move the grippers 46 closer to the center of the guiding tube 34. The shape of the bulges 48 and the channels 36 are adapted to avoid blockage between these components.

One will also note that the guiding tube 34 can include an extension 50 located on the side of the flap, equipped with a finger 50a which role will appear later.

The injection device 22 is still equipped with a locking system of the flap 26, not shown. This system allows for the passage of the compartment from its second closed position to an opened position, to be conditioned by the coupling of cap 20 with reference to the syringe 10. In this way, to secure the utilization of the injection device and to ensure that syringe 10 cannot be extracted from the compartment, in particular after an injection, only if the safety cap 20 has been replaced, a sensor, for example of an optical type, can be placed in the compartment in order to detect the presence of cap 20, at a height meaning that it is necessarily coupled with the syringe 10. This sensor can be advantageously linked to a latch, not shown, cooperating with the flap 26 when it is closed. The latch can be controlled electrically so as to be locked and to free the flap 26 only if the signal transmitted by the sensor indicates that the cap 20 is correctly placed on the syringe 10. Naturally, other types of sensors can be used to detect the presence of the cap. A locking system entirely mechanical could also be envisaged.

In an advantageous way, the injection device shown in the drawing also includes a locking system for syringe 10 in the compartment, which allows, when the syringe 10 has been completely inserted into the compartment, to release the syringe 10 only when the flap 26 is completely open.

To this effect, the internal wall of flap 26 includes a pin 52, forming a stop for a carriage 54, able to slide along the internal wall of flap 26. A first spring 56 exerts a force on the carriage 54 tending to bring it against the pin 52. The carriage 54 includes still a recess 58 arranged in such a way that the syringe, in particular its flange 16, can rest on it, when the syringe is inserted into the compartment. The carriage 54 includes still a lip 60 mounted retractable, stretching in direction of the inside of the compartment. The inside of the compartment includes still a second internal partition 62, adjusted inside of the ring 44 and including on its outside wall, a notch 64 with a shape matching lip 60. This notch is arranged in such a way that the finger 50a of extension 50 retracts when they meet in one direction, in this case, when the extension 50 moves in direction of the extremity of the flap. When the extension 50 moves in another direction, the lip is arranged in such a way that the finger 50a can escape from lip 60, without any interaction between these components. The lip 60 is positioned so as to cooperate with the notch 64 forming a mean of blockage.

The carriage 54 presents still, at the level of recess 58, a clip 66, more visible on the FIG. 2b. The clip 66 is movable radially and cooperates with a second spring 68, weaker than the first, exerting a force tending to move it towards the middle of the compartment. The pin 52 is arranged in such a way that, when the carriage 54 is resting against it, cooperates with the clip 66 and compresses the second spring 68 in such a way that the clip frees the recess 58. When the carriage 54 is not resting against the pin 52, the second spring moves the clip 66 above the recess 58. One will note that, in this last case, a space for the flange 16 remains between the recess 58 and the clip 66.

The second internal partition 62 presents a step 70 on which takes support the first spring 56. This step 70 is pierced with an opening susceptible to let through the extension 50 of the ring 44.

The different functions of the components that have been described above will now appear more clearly in the following description, made in reference to FIGS. 1 to 9.

FIG. 1 shows the injection device according to the invention, with the flap 26 open, in order to allow the insertion of a syringe 10 for injection. The position of arm 22 with reference to flap 26, results in the bulges 48 on grippers 46 of the ring 44 to be positioned in the first channels 36a. The extension 50 of the ring 44 positions the second internal partition 62 towards the extremity of flap 26 and the first spring 56 pushes the carriage 54 to rest against the pin 52.

During the insertion of the syringe 10 in the compartment, the flange 16 of the syringe will rest against the recess 58 of carriage 54 and the user, by compressing the first spring 56, brings the lip 60 to lock on the notch 64. When the flap 26 starts to close (FIG. 2), the pin 52 stops to cooperate with the clip 66, this one being pressed by the second spring 68 and locks the flange 16, preventing the syringe 10 to come out accidentally from the compartment. It is necessary to return completely the carriage 54 to rest against the pin 52 manually or by opening fully the flap 26 to free the syringe, eventually to remove it by force, but in any case intentionally.

By continuing the closing of flap 26, the arm 42 rotates at its two extremities and drives the ring 44 in translation. The grippers 46 leave the channels 36a and tighten in direction of the inside of the compartment so as to cooperate with the cap 20 of the syringe 10. Depending on the configuration and on the position of grippers 46, this cooperation can result in a pushing force on the edge of cap 20. The grippers can also bite into the cap 20 so as to the couple it with the ring 44. Advantageously, one combines grippers positioned differently, in order to have a better cooperation between them and the cap 20 and so as to couple the cap with the syringe in case of interruption of the closing. In this way, as shown the FIG. 3, the continuation of the closing of the flap allows to push the cap 20 and to decouple it from the syringe 10.

When the flap 26 is closed (FIG. 4), the bulges 48 return in the second channels 36b so as to stop cooperating with the cap 20. The cap extends beyond the device through the opening 32 which can advantageously be dimensioned so as to slightly hold the cap 20, so that it does not fall. The needle of the syringe remains recessed from the exterior surface of the device and the opening sufficiently small to prevent any contact with the patient. The latch of flap 26 is then locked, and it is not possible to open the flap, as long as the cap is not replaced onto the syringe 10.

Figure 5:
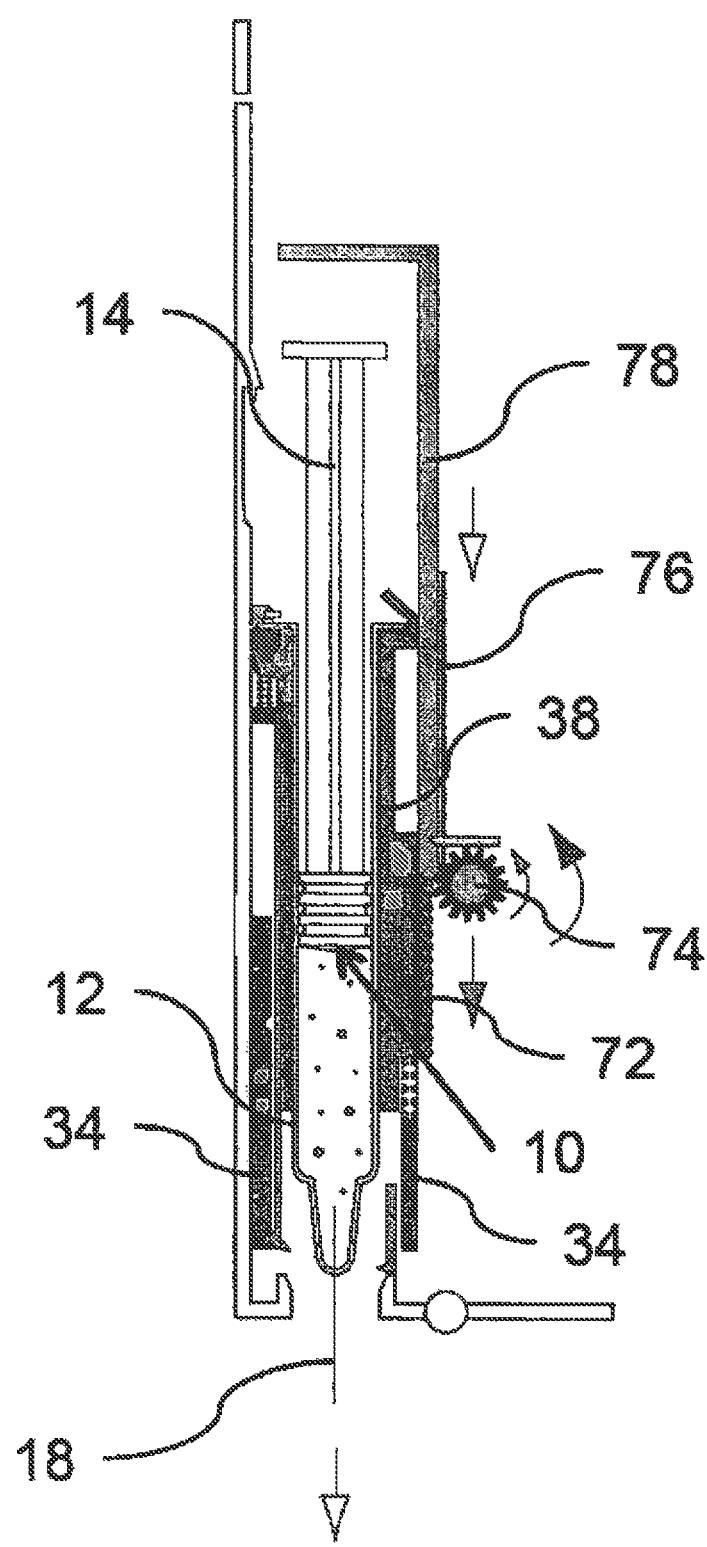
Figure 6:
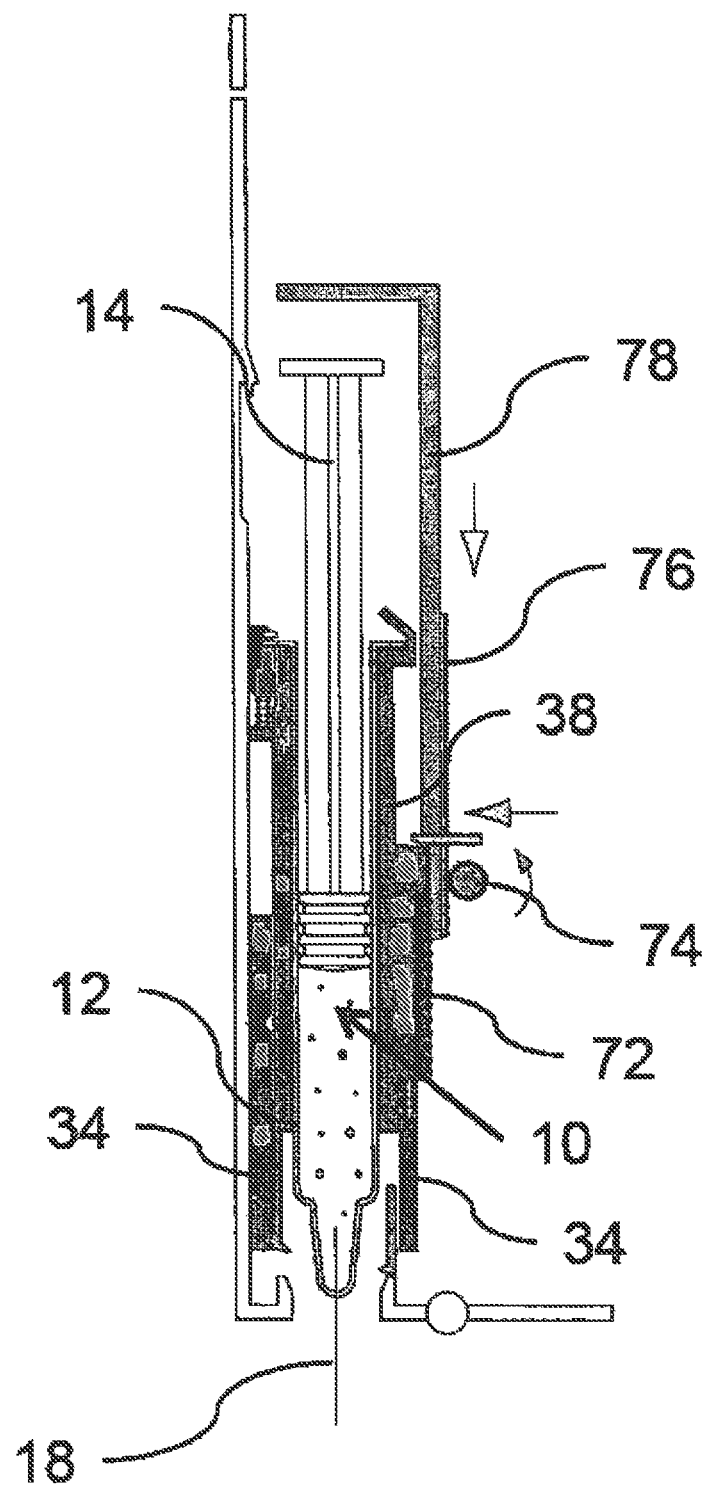

The patient can then position the device and trigger the injection (FIGS. 5 and 6). The syringe 10 is moved in the compartment, in direction of the opening 32, so that the needle 18 penetrates the skin of the patient. The piston 14 is activated in such a way that all or part of the product contained in the barrel 12 is injected. After the injection, the syringe 10 is retracted inside of the device and protected from any accidental contact with the patient or another person.

Figure 7:
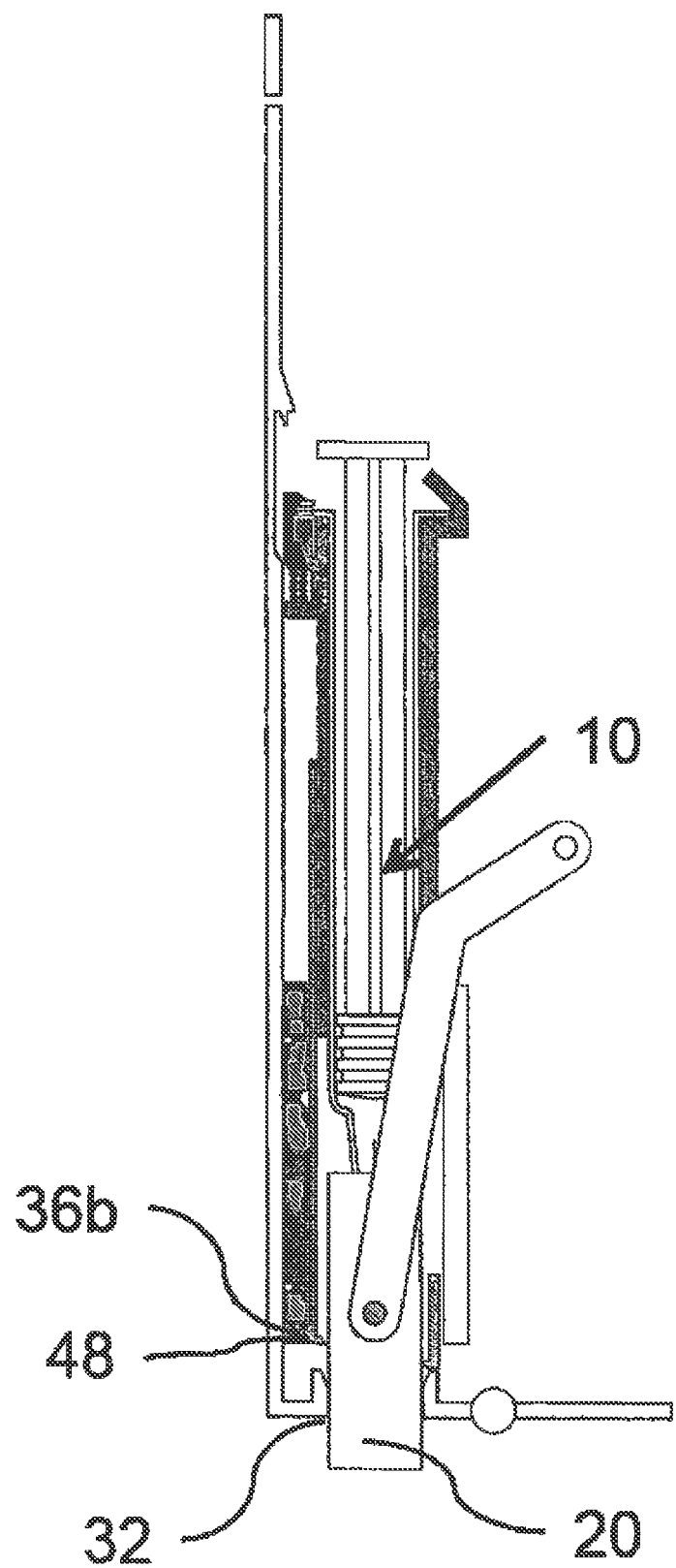
Figure 8:
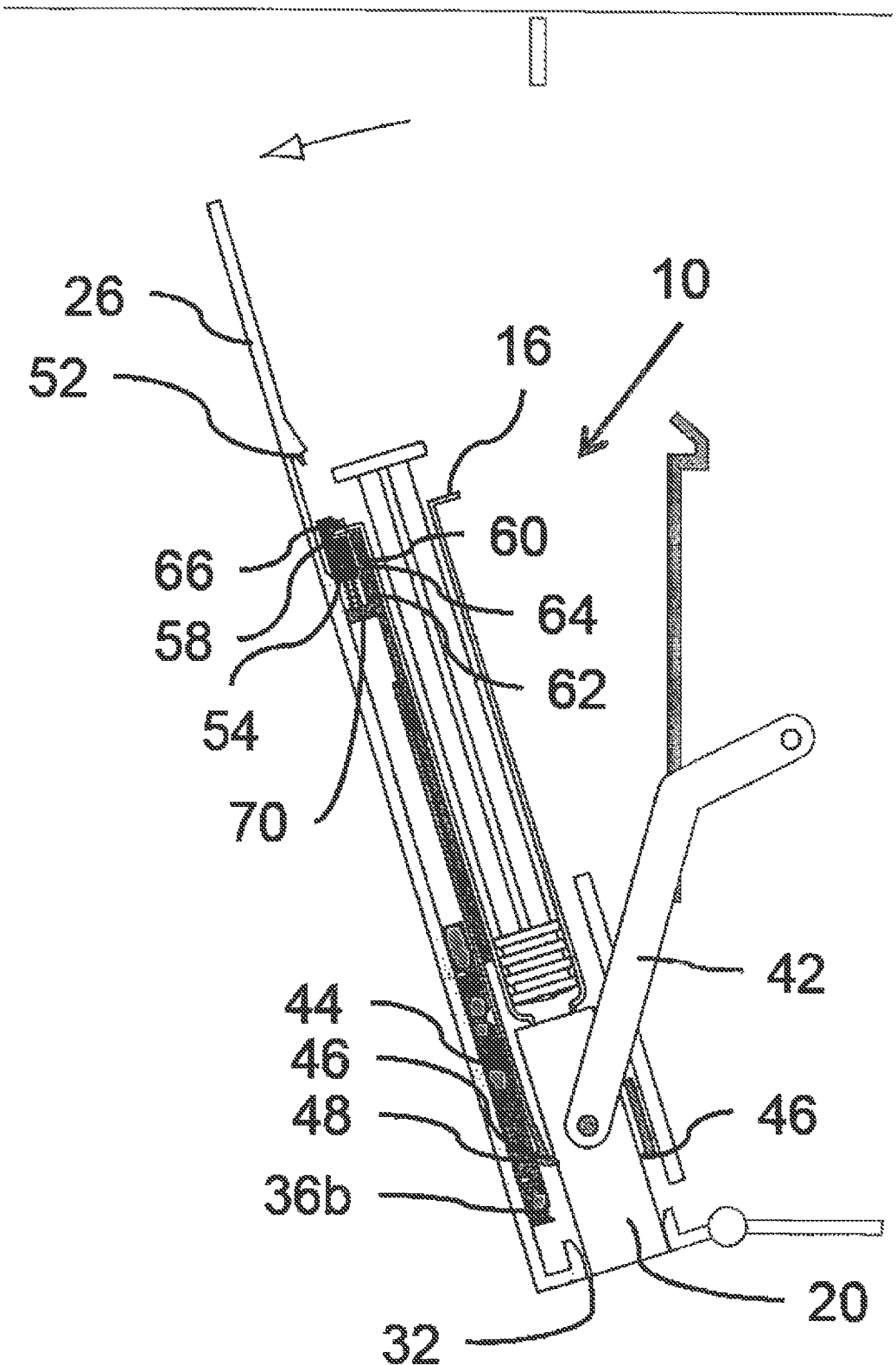

The bulges 48 are always in the second channels 36b, so that that the patient can freely insert the cap 20 into the opening 32 and to couple it with the syringe 10, in particular after an injection. The sensor then detects the presence of cap 20, which unlocks the latch and allows the opening of the flap (FIG. 7).

By opening the flap (FIG. 8), typically with a button acting on the latch, the movement of arm 42 brings back the ring 44 in a direction opposite to the opening 32. This drives the bulges 48 out of the second channel 36b and lead the grippers 46 to cooperate with the cap 20, which ensures that the cap cannot be decoupled from the syringe 10, during the extraction of the syringe. One will notice that, in this case, all the grippers 46 bite into the cap 20, because the bulges 48 are located in the second channels 36b.

Figure 9:
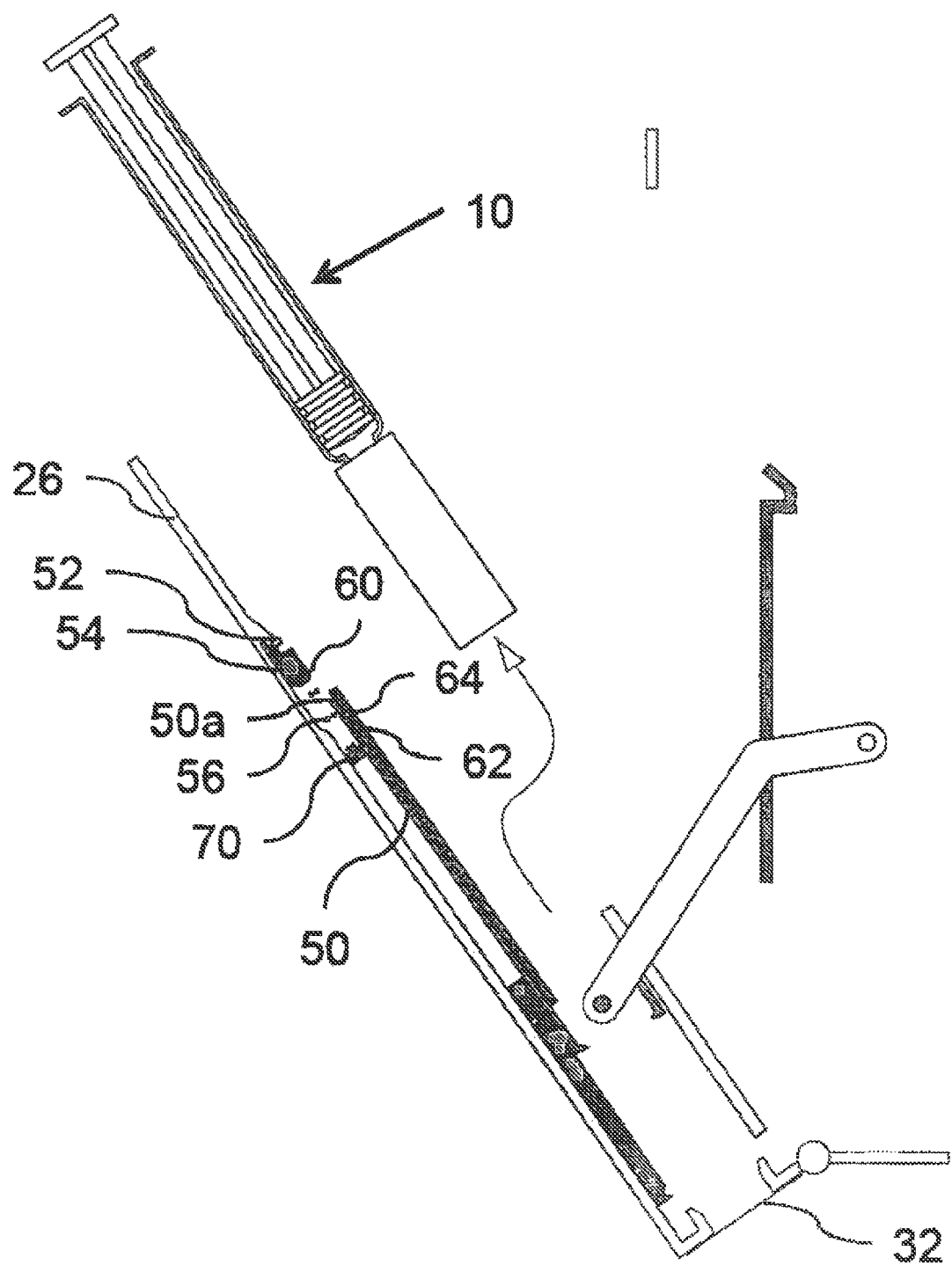

By continuing the opening of the flap 26, the finger 50a of extension 50 passes the opening of step 70 and pushes apart the second internal partition 62 so as to free the lip 60 from the notch 64. The carriage 54 is then freely subjected to the action of the first spring 56, which pushes it in the direction of the pin 52. This results in bringing the syringe 10 towards the exit of the compartment, because the flange 16 is still locked between the recess 58 and the clip 66. Finally, when the carriage 54 stops against the pin 52, the clip 66 frees the flange 16 and the patient can remove the syringe 10, protected by cap 20, in complete safety (FIG. 9).

In this way, the detachment system of cap 20 with reference to the syringe 10, coordinated with the closing of flap 26, on one hand, and the control of the unlocking of the closing latch of the flap 26, on the other hand, allows and ensures that the patient inserts and removes the syringe with its cap. In this way it is impossible to get injured by the needle, before, during and after the injection.

The sensor detecting the presence of cap 20 can be used to condition the trigger of an injection to the retraction of the cap, in such a way that the injection cannot be triggered if the cap is still present in the opening 32.

For the realization of the injection, it is necessary, in a first stage, to displace completely the syringe in the direction of the opening, so as to make the needle penetrate into the patient's skin. In a second stage, to activate the piston so as to expel the liquid contained in the syringe and to actually inject it.

For the first step, one can see, on FIGS. 5 and 6, that a rack 72 is mounted coupled with the internal partition 38. For the passage of the rack 72, an opening can be arranged in the guiding tube 34. This rack cooperates at a first level of pinion 74 driven by a motor, not shown.

The pinion 74 includes advantageously a second level, placed so as to cooperate with a second rack 76 mounted on a push-piston 78. The first and the second racks are arranged in such a way that, during the rotation of pinion 74, the first then the second level cooperate successively and respectively with the racks 72 and 76. In this way are successively carried out the first and second injection steps. In an advantageous way, a single motor is used to carry out these two operations. One can eventually play with the teeth on the two levels of pinion and racks as well as on the rotation speed of motor to adapt the driving speed.

In a second embodiment not shown, the first and the second racks can be driven by two different motors. One will also note that the piston could be driven directly by a lead screw cooperating with the disc ending generally the piston, instead of a drive with a push-piston.

The injection device according to the invention is equipped with electronic means allowing to control the different operations carried out during the injection, in particular the activation of motors for the displacement of the syringe and for the activation of the piston. The electronic means are also used, as mentioned above, to control the locking of the latch depending on the presence of the cap on the syringe.

The electronic means are advantageously programmable. The programming can be done eventually by a direct interface, including a screen and control buttons, or by an indirect interface, located at a distance from the apparatus and communicating with the device by Internet or by telephone connection.

The electronic means can in this way be programmed to manage injections of doses, formed by portions of the syringe's content. Since the device is programmed to identify the product present in the syringe and its concentration, and the dose of medication to administer, the device determines the quantity of product to inject and, at the time of injection, to administer it. The device can also integrate an electronic sensor, for example optical, to detect the position of the piston.

The electronic means can, in an advantageous way, be used to monitor and control the correct adherence to the treatment and, eventually, remind the patient of the time for injections. In preference, the data related to the patient and to his treatment are stored at distance, on a server with which the device communicates.

Figure 10:
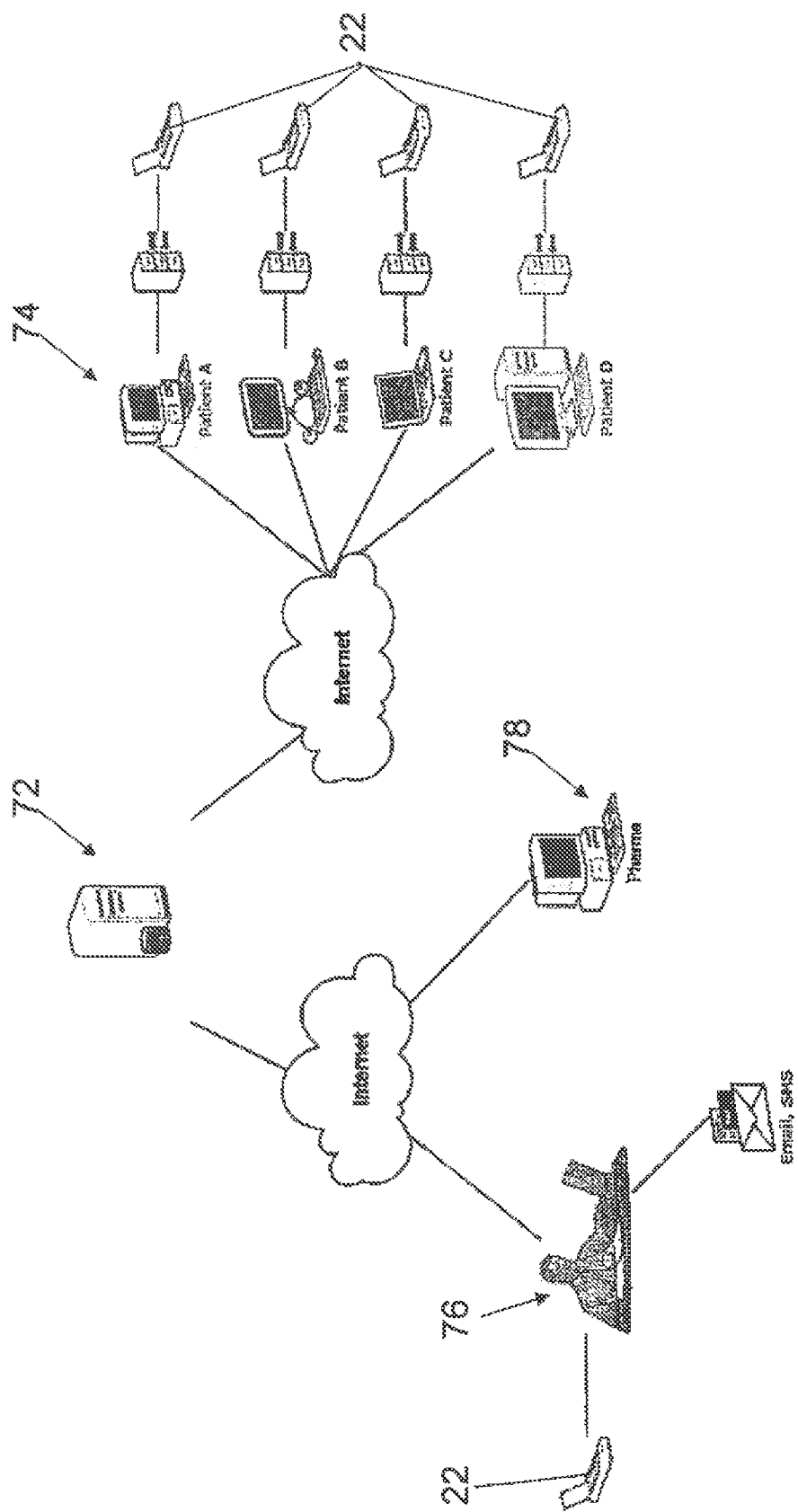
Figure 12:
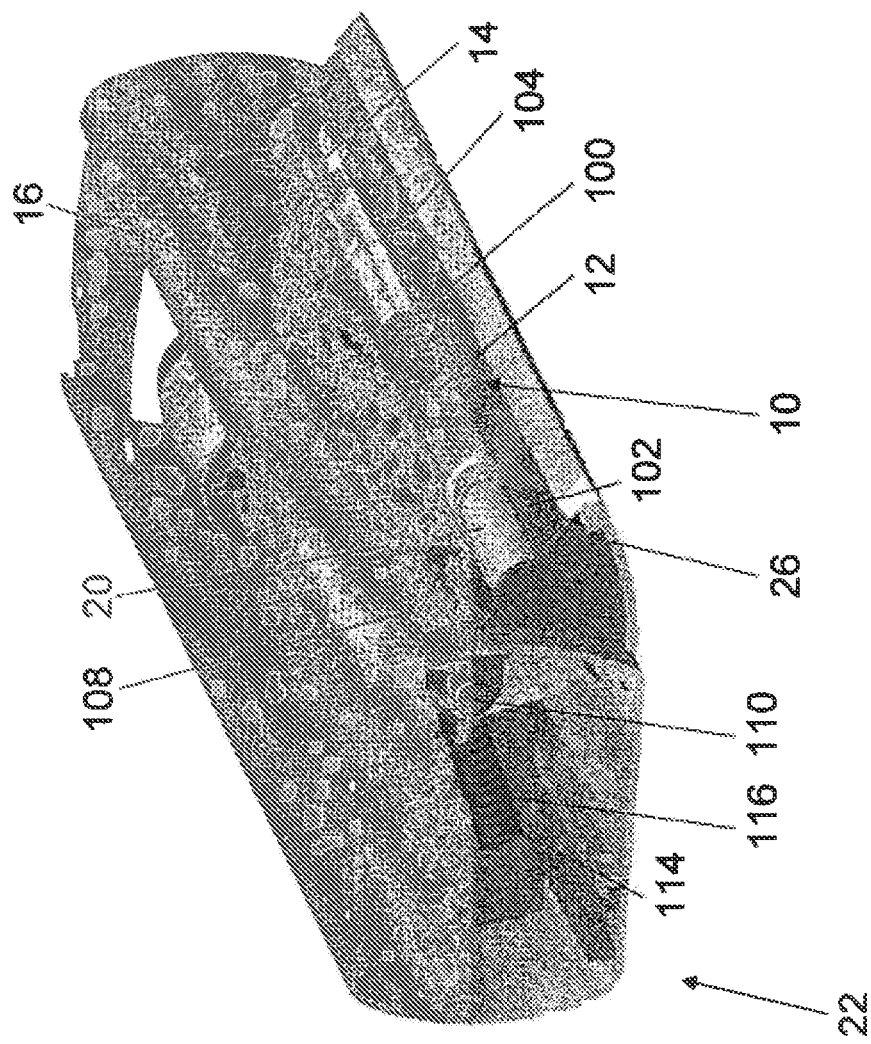
Figure 13:
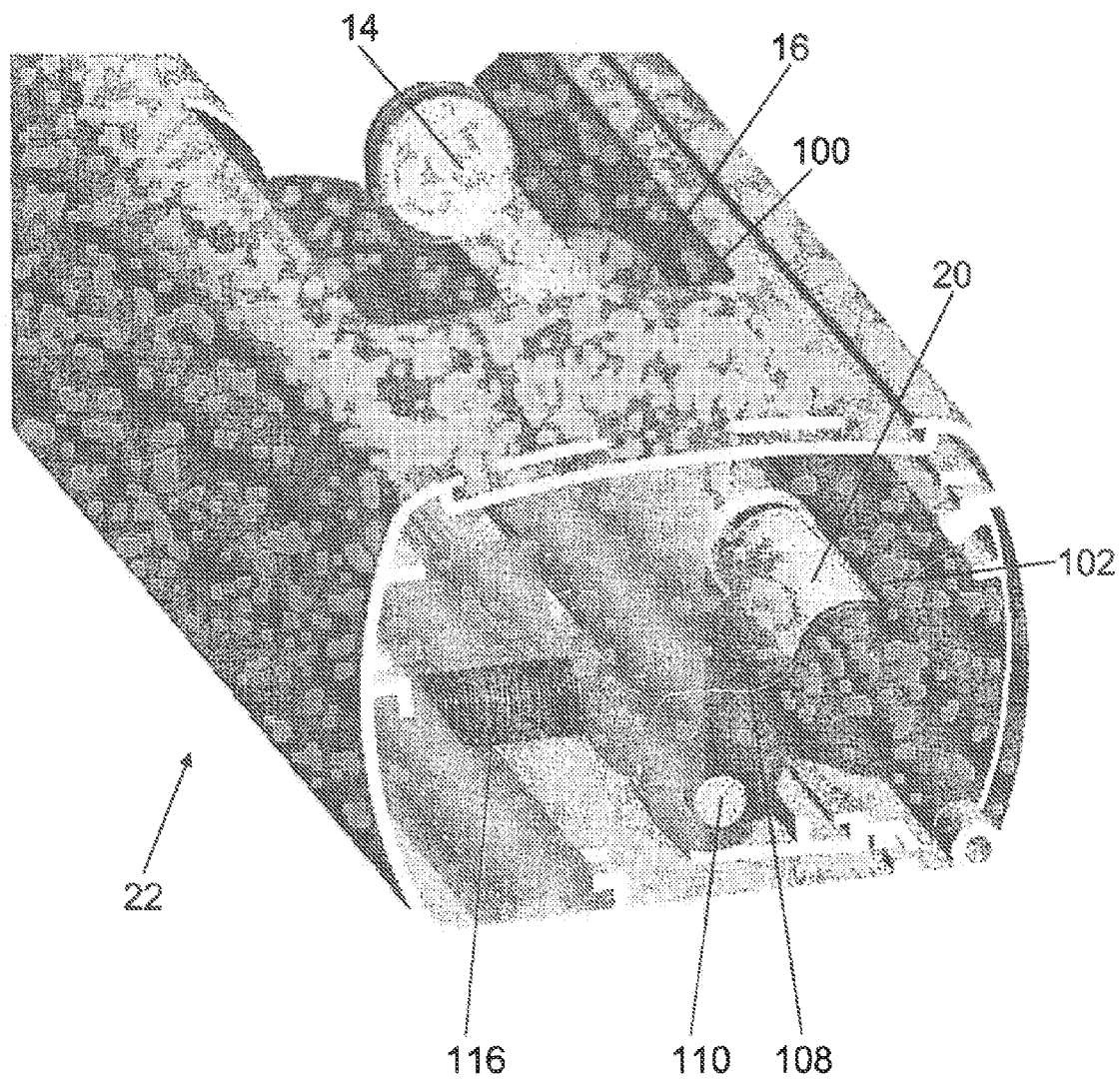
Figure 14:
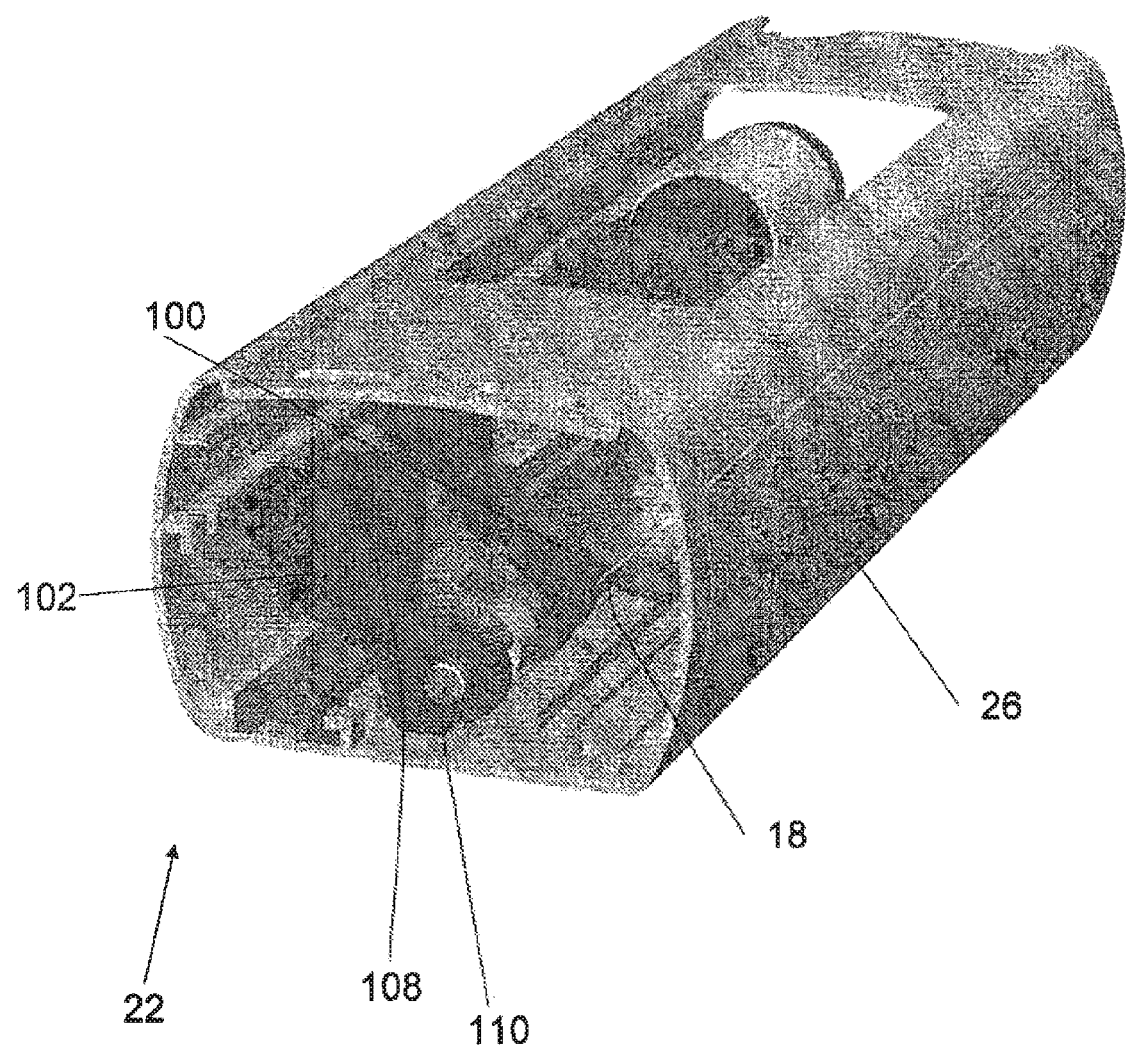
Figure 15:
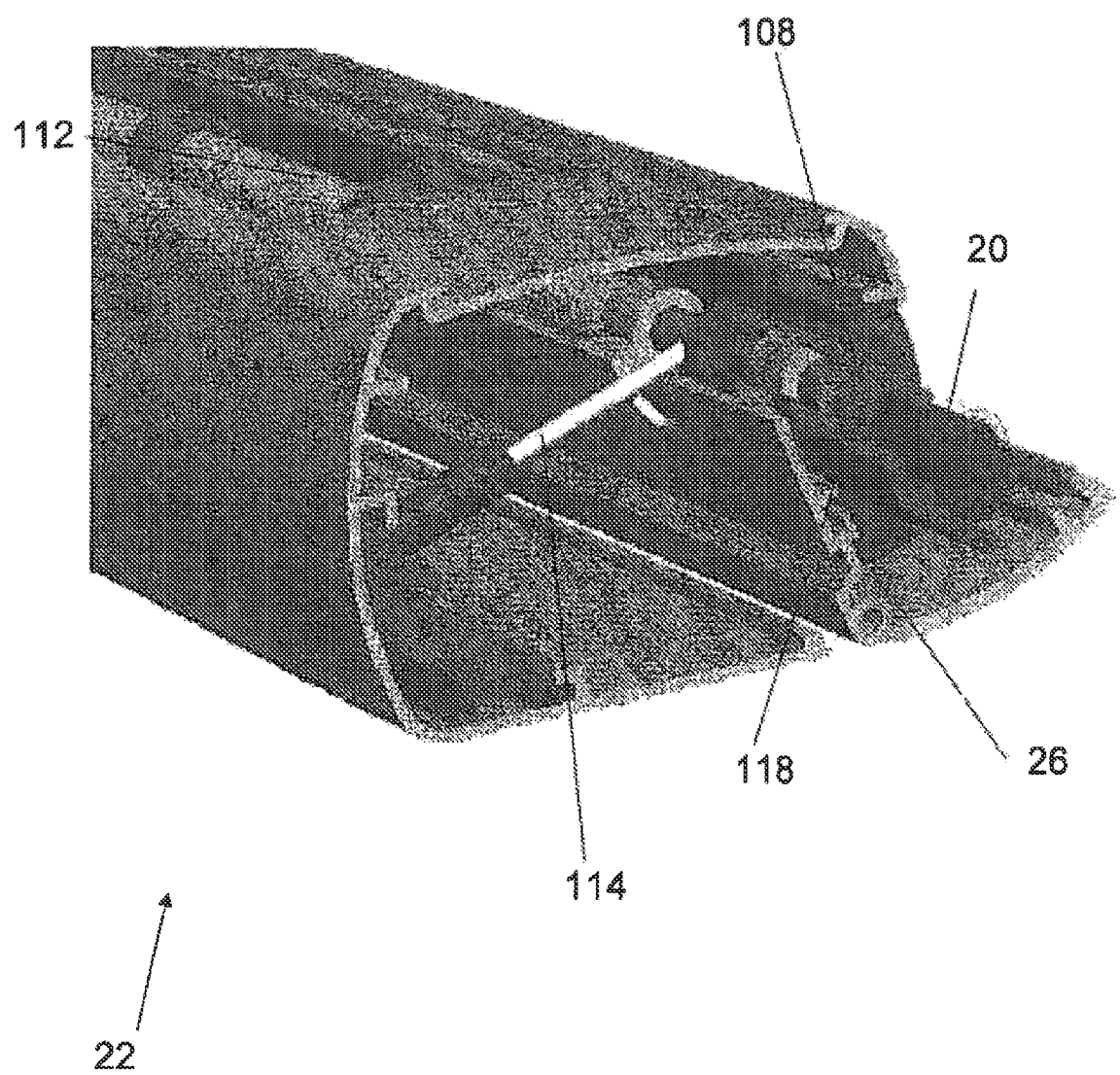

In this way, FIG. 10 illustrates a management system and control of injection protocols, including:
 a server 72 storing data related to the patient and to his treatment, and
 at least an injection device 22 as described previously, including means of connecting at distance to a server.

Represented on the figure are devices 22 for patients A, B, C and D.

The electronic means are arranged to:
 record the injections history,
 monitor and control the adherence to the treatment and, eventually, remind the patient of the time for injections,
 transmit to the server the aforementioned history,
 receive and process information transmitted by the server.

In preferred embodiments, the electronic means can, furthermore, be programmed to detect and control the nature and expiry date of the syringe. As shown in FIG. 11, this information can be coded as 2D barcodes, taking the shape of a label 80 of small dimension, occupying a reduced portion of the syringe, in particular a reduced portion of its circumference. A reader of this type of barcode is foreseen in the injection device. To avoid any orientation problem of the syringe in relation to the reader, a number of labels 80 are placed on the perimeter of the syringe. In order to reduce further the orientation problem, a number of labels 80 are placed staggered on the perimeter, according to two annular lines. One could foresee more lines, the labels being shifted with reference to the others, so that any given angular portion of the barrel of the syringe does include a label. The annular lines according to which are placed the labels can be adjacent, so that the labels touch one other (or almost) by their corners, or be separated. The device including one or several readers to read the barcodes.

In this way, whatever the position of the syringe in the device, the reader can always read at least one barcode. The barcodes can be printed with an ink invisible in day light, but sensible to UV light for example, a corresponding light source being placed in the injection device to make the barcodes visible.

Furthermore, the electronic means can as well be used to regulate the injection parameters of speed or of time. One can still note that the electronic means can allow or prevent the injection depending on the detection or on the absence of the cap and on the presence of the skin.

For example, one can foresee that the injection device connects to the server through a mobile phone, communicating wirelessly with the injection device. One can also consider that the device has to be recharged electrically by being connected to a computer 74, by a USB connection and that, at this occasion, if the computer is connected to Internet, the device connects automatically to the server. In both cases, the electronic means can be programmed to provide to the server identification elements, that allow the recognition of the device and of the treatment associated with the patient. The server can then load from the device, the injections history. This history can then be consulted by the doctor 76, eventually when he connects to the server or, by sending an email with a file that includes the history. The doctor can, if necessary, modify the injection program of the patient or the dosage, these modifications being transmitted to the device during its next connection.

The pharmaceutical companies 78 can also have the possibility to connect to the server 72, for example to modify data related to the injected product or to prevent the utilization of certain syringes identified by their lot number or serial number, in particular to ensure that a syringe is not used twice.

The electronic means can be programmed to provide reminder signals to the patient, in order to warn of the time when he has to carry out the next injection. These signals can be audible, visual, or consisting in messages displayed on the device screen. The reminders can as well be sent to the patient from the server, by email or by SMS. Depending on the treatment and disease, the device can as well send an alarm signal when an injection is not carried out or after a certain delay during which the device has not been used.

Naturally, the different communication functions of the device with the server or with other apparatus can be activated or deactivated, either by the suppliers of the device or by the doctors treating the patient.

The FIGS. 12 to 15 relate to an additional embodiment of an injection device 22 according to the invention, in which the retraction of the cap is managed by the electronic means, after the closing of flap 26.

As in the first embodiment, the injection device 22 includes a compartment closed by an articulated flap 26. The compartment is susceptible to evolve from a first open position for the insertion and the removal of the syringe 10, and a second closed position for the realization of the injection. In this variant, the flap 26 opens laterally with reference to the device, which is according to an axis parallel to the longitudinal axis of the device. The inside of the compartment includes a tray in two parts, with the shape of a gutter, which curvature is noticeably identical to that of conventional syringes, for the type of injection considered. A first part 100 is intended to receive the barrel 12 and the piston 14 of the syringe 10 when the syringe is inserted into the compartment, whereas a second part 102 is intended to receive the cap 20 protecting the needle 18.

The first part 100 is designed to allow a precise insertion and without play of the syringe 10 in the tray. A shoulder 104 is foreseen to provide a support to the flange 16, in order to maintain the barrel 12 during the activation of piston 14. Typically, the first part 100 includes at least an area elastically deformable to maintain by clipping the barrel of the syringe 10. The specialist can foresee other systems for maintaining the syringe, such as a lever positioned by a spring and maintaining the syringe in place. The first part 100 can, furthermore, include a system allowing the activation of the piston 14 during an injection.

The first part 100 is mounted movable in translation with reference to the second part 102, inside the device. One can, for example, use a pinion and rack drive, of the type described in the first embodiment, or a lead screw.

The second part 102 is mounted movable in rotation with reference to the first part 100. The second part 102 is susceptible to occupy a first position in which it extends the first part 100, in such a way that the user can introduce the barrel 12 of the syringe 10 in the first part 100, whereas the cap 20 positions at the level of the second part 102. Particularly, the second part 102 is in this first position when the compartment is open. As one will understand later, the second part 102 is also susceptible to occupy at least a second position in which it is totally located outside of the translation path of the first part 100.

The second part is equipped with a tightening mechanism of the cap, including a jaw 108 capable to cooperate with the cap 20 by enclosing it. The jaw 108 is arranged so as to leave free the cap 20 when the flap 26 is open, which is when the compartment and the second part 102 are in their first position. Furthermore, the jaw 108 is arranged to be coupled with the cap when the flap is closed. In preference, the passage of the jaw 108 from the free position to the enclosed position is done automatically.

FIGS. 12 to 15 illustrate the second part of the tray. One can in particular see an axis 110 around which rotates the second part 102. This axis 110 is distinct from the axis around which rotates the flap 26. A lead screw 112 is located in the extension of the axis 110, to drive in translation the first part 100. The lead screw 112 is independent of the axis 110. A cylinder 114 equipped with a spring 116 (shown only in the FIGS. 12 and 13) is positioned between the inside of the injection device and the axis 110. The cylinder 114 is mounted articulated on the injection device and on the axis 110, which it drives in rotation. The cylinder 114 and the spring 116 are arranged so as to exert on the axis 110 a force tending to open the flap 26 of the compartment. The opening and the closing of flap 26 drive the rotation of the axis 110.

In the example illustrated, the jaw 108 is susceptible to evolve in translation with reference to the axis 110. It can in this way present an oblong opening inside which passes through the axis 110. The axis presents an eccentric portion, such as a plane 118 at the level of the oblong opening. The jaw is maintained pressed on the plane by a spring. In this way, depending on the relative orientation of the plane with reference to the oblong opening, the jaw moves in translation with reference to the axis, so that its rotation moves the jaw 108 defining the free and enclosed positions. The jaw can include a rubber pad to improve the retention of the cap.

In this second embodiment, when the flap 26 is open, the user inserts a syringe 10 in the compartment, including the first part 100 and the second part 102 located in the extension of each other, as shown in the FIG. 11. The syringe 10 is clipped without play on the first part 100. By closing the flap 26, the jaw 108 encloses automatically the cap. The spring 116 is compressed and a locking system on the flap allows it to maintain the compartment in a closed position.

Then, automatically, the first part 100 of the tray translates, whereas the second part 102 remains fixed and the cap 20 being maintained by the jaw 108. As a result, the cap 20 is decoupled from the rest of the syringe. The first part 100 translates until the needle 18 is totally removed from cap 20, defining an extreme position of the syringe 10. The translation stroke of the first part 100 is thus superior to the length parts housed in the cap 20.

The second part 102 of the tray can then, in view of an injection, rotate according to the axis 110 to its second position, so as to clear the cap 20 from the path of the syringe and in such a way that the second part 102 does not interfere with the moving of the first part. One will note that, during its rotation, the second part 102 drives the jaw 108 and the axis 110, the relative position of these two last components being fixed, so as to always maintain the cap.

When the second part 102 of the tray reaches its second position, the injection can be carried out by moving at first the barrel 12 and the piston 14 of the syringe with the lead screw, then by moving the piston 14, following the example which has been described in reference to the first embodiment.

After the injection, the barrel 12 and the piston 14 of the syringe retract in the device, until the extreme position defined previously. The second part 102 can then recover its first position and be replaced in the extension of the first part 100, the cap 20 being then in the axis of the barrel of the syringe. The first part 100 then translates again so as to couple the cap with the syringe. The flap 26 can then be unlocked and opened and the syringe unclipped, with the cap 20 that protects the needle 18.

A skilled person will be able to easily and without it being necessary to describe, foresee the motors and actuators for the movement of the different components. These movements are managed by electronic means, as described above. One will note still that these operations can be made automatically since the flap 26 is detected as closed, but they can also be triggered by a pressure on a control organ.

Sensors and electronic or electromechanical safety systems can be foreseen so as to ensure the correct operational sequence, the whole being managed by the aforementioned electronic means. In this way, the detachment of the cap is conditioned by the passage of the compartment to its closed position and the opening of compartment is conditioned by the coupling of the cap. In particular, the operations for the retraction of the cap can be carried out only if a sensor detects that the flap 26 is closed and locked. On the opposite, the unlocking and the opening of flap 26 are allowed only if another sensor confirms the presence of the cap on the syringe. Furthermore, the rotation of the second part 102 is possible only if the first part 100 is in its extreme position. The movement of the first part 100 is possible only when the second part 102 is in its second position.

This embodiment presents the advantage that the complete operation for the retraction of the cap is performed automatically, without any manual intervention. The cap remains inside of the injection device, which avoids its loss when removed.

One will note that the embodiment described above can be easily adapted, in particular in what relates to the movement of the first and second parts of the tray. Indeed, it is obvious that it is sufficient that these two parts be movable in reference to one another, according to two orthogonal directions, in order to allow the decoupling of the cap and its release/engagement. One could in this way envisage that the two parts move according to two translation movements. In particular in this last case, the tightening of the cap by the jaw 108 can be managed electromechanically, that is dictated by the detection of the locked position of flap 26 by a sensor, and that the release of the cap is triggered during the unlocking of flap 26.

In this way it is proposed an improved injection device, intended to be used repeatedly and allowing the utilization of disposable syringes, preventing that the user has to handle the syringe with the bare needle. The device is also programmable, advantageously at distance, for an easy and efficient bilateral follow-up, meaning that the caregiver as well as the patient can consult, receive and transmit information related to the injections program.

The description above has been given as a non limiting illustration of the invention and the skilled person will be able to foresee other embodiments for achieving the functions described, without going over the scope of the claimed invention below. One could in this way foresee that the retraction of the cap be entirely managed by electronic means, after the closing of the flap.

The invention claimed is:

1. An injection device, comprising:
    a compartment articulated in reference to the device to receive a syringe with stake needle protected by a protection cap coupled with the syringe, the compartment being susceptible to evolve from a first open position for the insertion and the removal of the syringe, and a second closed position for the realization of the injection; and
    a detaching system intended to cooperate with the cap of the syringe to perform a detachment of said cap from the syringe, the detachment being conditioned by the passage of the compartment to its second position, the passage of the compartment from the second to the first position is conditioned by the coupling of the cap to the syringe.

2. The injection device of claim 1, wherein the detachment is carried out automatically during the passage from the first to the second position.

3. The injection device of claim 2, wherein the detaching system includes grippers arranged to cooperate with the cap, said grippers being driven in translation with reference to the cap, depending on the position of the compartment, from a first and a second position, the grippers being arranged so as not to cooperate with the cap when they are in the first and second position, and to cooperate with the cap when they are between the first and second position.

4. The injection device of claim 1, wherein the injection device is arranged so as to leave accessible the cap after the detachment, for a manual retraction, whereas the needle remains inaccessible inside the device.

5. The injection device of claim 2, wherein the injection device is arranged so as to leave accessible the cap after the detachment, for a manual retraction, whereas the needle remains inaccessible inside the device.

6. The injection device of claim 3, wherein the injection device is arranged so as to leave accessible the cap after the detachment, for a manual retraction, whereas the needle remains inaccessible inside the device.

7. The injection device of claim 1, wherein the injection device is arranged in such a way that, after an injection, the needle is located inside the device in an inaccessible way, the cap can be coupled with the syringe from the outside.

8. The injection device of claim 2, wherein the injection device is arranged in such a way that, after an injection, the needle is located inside the device in an inaccessible way, the cap can be coupled with the syringe from the outside.

9. The injection device of claim 3, wherein the injection device is arranged in such a way that, after an injection, the needle is located inside the device in an inaccessible way, the cap can be coupled with the syringe from the outside.

10. The injection device of claim 4, wherein the injection device is arranged in such a way that, after an injection, the needle is located inside the device in an inaccessible way, the cap can be coupled with the syringe from the outside.

11. The injection device of claim 1, further comprising a sensor arranged to detect the presence of said cap coupled with the syringe, and said sensor controlling the locking of the compartment in its second position, the compartment being maintained locked while that sensor does not detect the presence of said cap.

12. The injection device of claim 2, further comprising a sensor arranged to detect the presence of said cap coupled with the syringe, and said sensor controlling the locking of the compartment in its second position, the compartment being maintained locked while that sensor does not detect the presence of said cap.

13. The injection device of claim 3, further comprising a sensor arranged to detect the presence of said cap coupled with the syringe, and said sensor controlling the locking of the compartment in its second position, the compartment being maintained locked while that sensor does not detect the presence of said cap.

14. The injection device of claim 1, wherein a maximum open position is defined, including a locking system for syringe in the compartment, arranged in such a way that, when the syringe has been completely inserted in the compartment, the syringe be locked in the compartment as long as the latter is not back to its maximum open position.

15. The injection device of claim 2, wherein a maximum open position is defined, including a locking system for syringe in the compartment, arranged in such a way that, when the syringe has been completely inserted in the compartment, the syringe be locked in the compartment as long as the latter is not back to its maximum open position.

16. The injection device of claim 3, wherein a maximum open position is defined, including a locking system for syringe in the compartment, arranged in such a way that, when the syringe has been completely inserted in the compartment, the syringe be locked in the compartment as long as the latter is not back to its maximum open position.

17. The injection device according to claim 14, wherein said locking system for the syringe cooperates with a spring arranged so as to push the syringe in direction of the compartment exit when the compartment reaches its maximum open position.

18. The injection device of claim 1, wherein the detachment system includes a tray in two parts:
    a first part intended to receive and to maintain the syringe, and mounted in translation with reference to the device,
    a second part intended to receive the cap,
    said first and second parts being movable with reference one another, according to two orthogonal directions,
    wherein the aforementioned second part is equipped with a tightening mechanism on the cap, including a jaw arranged so as to occupy a free position where said jaw let free the cap when the compartment is in its first position, so as to occupy an encloses position where said jaw encloses firmly the cap when the compartment is in its second position.

19. The injection device of claim 18, wherein the jaw is mounted on an eccentric driven in rotation during the passage of the compartment from one to the other of its first and second position, the rotation of said eccentric driving a movement of jaw defining the free and enclosed positions of the jaw.

20. The injection device according of claim 18, wherein said first part and said second part are movable in translation in reference to one another according to a stroke superior to the length of the parts housed in the cap, in such a way that the needle be totally removed from the cap.

21. The injection device according of claim 19, wherein said first part and said second part are movable in translation in reference to one another according to a stroke superior to the length of the parts housed in the cap, in such a way that the needle be totally removed from the cap.

22. The injection device of claim 18, further comprising electronic means and actuators to displace the first part and second part of the tray, wherein said electronic means are programmed to control the actuators, in such a way that, when a syringe is housed in the compartment and that the latter is in its first position, carry out the following steps:

shift the first part and second part of the tray in reference to one another whereas the cap is maintained by the tightening mechanism, the cap being decoupled from the remaining of the syringe, until an extreme position where the needle is totally removed from the cap, displace the first part and second part of the tray in reference to one another so as to release the cap from the path of the syringe, in view of an injection, carry out the injection by moving at first the syringe then by moving its piston, after the injection, return the syringe to the extreme position, displace the first part and second part of the tray in reference to one another so as to bring the cap in the axis of syringe, translate the first part and second part of the tray in reference to one another whereas the cap is maintained by the tightening mechanism, the cap being coupled again to the rest of the syringe.

23. The injection device of claim 19, further comprising electronic means and actuators to displace the first part and second part of the tray, wherein said electronic means are programmed to control the actuators, in such a way that, when a syringe is housed in the compartment and that the latter is in its first position, carry out the following steps:

shift the first part and second part of the tray in reference to one another whereas the cap is maintained by the tightening mechanism, the cap being decoupled from the remaining of the syringe, until an extreme position where the needle is totally removed from the cap, displace the first part and second part of the tray in reference to one another so as to release the cap from the path of the syringe, in view of an injection, carry out the injection by moving at first the syringe then by moving its piston, after the injection, return the syringe to the extreme position, displace the first part and second part of the tray in reference to one another so as to bring the cap in the axis of syringe, translate the first part and second part of the tray in reference to one another whereas the cap is maintained by the tightening mechanism, the cap being coupled again to the rest of the syringe.

24. The injection device of claim 20, further comprising electronic means and actuators to displace the first part and second part of the tray, wherein said electronic means are programmed to control the actuators, in such a way that, when a syringe is housed in the compartment and that the latter is in its first position, carry out the following steps:

shift the first part and second part of the tray in reference to one another whereas the cap is maintained by the tightening mechanism, the cap being decoupled from the remaining of the syringe, until an extreme position where the needle is totally removed from the cap, displace the first part and second part of the tray in reference to one another so as to release the cap from the path of the syringe, in view of an injection, carry out the injection by moving at first the syringe then by moving its piston, after the injection, return the syringe to the extreme position, displace the first part and second part of the tray in reference to one another so as to bring the cap in the axis of syringe, translate the first part and second part of the tray in reference to one another whereas the cap is maintained by the tightening mechanism, the cap being coupled again to the rest of the syringe.

25. A management and control system of injections protocol, comprising:

a server storing data related to the patient and to his treatment, and at least an injection device according to claim 18 to carry out the injections, including connection means to connect remotely the server and an electronic means, wherein said electronic means are arranged to record the injections history, monitor and control the adherence of treatment and, eventually, remind patient of the time for injections, transmit to the server said injections history, receive and process information transmitted by the server.

26. The management and control system of claim 25, wherein said electronic means are furthermore arranged to detect and control the nature and expiry date of a syringe.

27. The management and control system of claim 26, wherein said electronic means are furthermore arranged to regulate the injection parameters of speed or of time.

28. The management and control system of claim 25, wherein said electronic means are furthermore arranged to regulate the injection parameters of speed or of time.

29. The management and control system according to claim 25, wherein the connection means are arranged so as to connect wirelessly said automatic injection device to a mobile phone, said mobile phone connecting the automatic injection device to the server.

30. The management and control system according to claim 29, further comprising a syringe comprising a plurality of 2D barcodes, placed on an annular line or placed staggered according to at least two annular lines located on the perimeter of the syringe.

31. The management and control system according to claim 25, further comprising a syringe comprising a plurality of 2D barcodes, placed on an annular line or placed staggered according to at least two annular lines located on the perimeter of the syringe.

* * * * *